United States Patent [19]
Garvey et al.

[11] Patent Number: 6,143,734
[45] Date of Patent: *Nov. 7, 2000

[54] NITROSO ESTERS OF β-OXO-AMIDES AND ARYL PROPIONIC ACID DERIVATIVES OF NON-STEROIDAL ANTIINFLAMMATORY DRUGS

[75] Inventors: David S. Garvey; L. Gordon Letts, both of Dover; H. Burt Renfroe, Wellesley; Sang William Tam, Dover, all of Mass.

[73] Assignee: NitroMed, Inc., Bedford, Mass.

[*] Notice: This patent is subject to a terminal disclaimer.

[21] Appl. No.: 09/495,251

[22] Filed: Jan. 31, 2000

Related U.S. Application Data

[60] Continuation of application No. 09/235,802, Jan. 22, 1999, Pat. No. 6,043,232, which is a division of application No. 08/899,238, Jul. 23, 1997, abandoned, which is a division of application No. 08/425,090, Apr. 19, 1995, Pat. No. 6,051,588.

[51] Int. Cl.$^7$ .................. A61K 31/407; A61K 31/4245; C07D 487/04; C07D 271/04
[52] U.S. Cl. .................. 514/159; 514/166; 514/364; 514/413; 514/513; 514/539; 514/619; 514/622; 548/126; 548/453; 558/256; 560/47; 560/48; 560/49; 560/71; 564/163; 564/167
[58] Field of Search .................. 514/159, 166, 514/364, 413, 513, 539, 619, 622; 548/126, 453; 558/256; 560/47, 48, 59, 71; 564/163, 177

[56] References Cited

U.S. PATENT DOCUMENTS

| | | | |
|---|---|---|---|
| 4,556,672 | 12/1985 | Kadin | 514/414 |
| 5,621,000 | 4/1997 | Arena et al. | 514/411 |
| 5,700,947 | 12/1997 | Soldato | 548/491 |
| 5,703,073 | 12/1997 | Garvey et al. | 514/226.5 |
| 5,780,495 | 7/1998 | Del Soldato | 514/413 |
| 6,043,232 | 3/2000 | Garvey et al. | 514/159 |
| 6,043,233 | 3/2000 | Garvey et al. | 514/159 |
| 6,051,588 | 4/2000 | Garvey et al. | 514/364 |
| 6,057,347 | 5/2000 | Garvey et al. | 514/364 |

FOREIGN PATENT DOCUMENTS

| | | |
|---|---|---|
| 0658559 | 6/1995 | European Pat. Off. . |
| WO 93/09806 | 5/1993 | WIPO . |
| 9404484 | 3/1994 | WIPO . |
| 9412463 | 6/1994 | WIPO . |
| WO 94/12463 | 6/1994 | WIPO . |
| 9509831 | 4/1995 | WIPO . |
| 9530641 | 11/1995 | WIPO . |
| 9716405 | 5/1997 | WIPO . |
| 9731654 | 9/1997 | WIPO . |
| 9809948 | 3/1998 | WIPO . |

OTHER PUBLICATIONS

Carty et al., *Agents Actions*, 39:157–165 (1993).
Conforti et al., *Agents Actions*, 40:176–180 (1993).
Cuzzolin et al., *Pharmacol. Res.*, 29(1):89–97 (1994).
Goodman and Gilman's, *Pharmacological Basis for Therapeutics*, (8th Ed.):630–681 (1993).
Reuter et al., *Life Sci.*, 55(1):PL1–PL8 (1994).
Reuter et al., *Immunology, Microbiology and Inflam. Disorders*, A759 (1994).
Soll et al., *Annals of Internal Medicine*, 114:307–319 (1991).
Wallace et al., *Eur. J. Pharmacol.*, 257:249–255 (1994).
Wallace et al., *Gastroenterology*, 106(4):Part 2A208AGA Abstracts (1994).
Wallace et al., *Gastroenterol. and Hepatol.*, 9:S40–S44 (1994).
Wallace et al., *Novel Molecular Approaches to Anti–Inflammatory Theory; Birkäuser Verlag*, Basel:121–129 (1995).
Wallace et al., *Gastroenterology*, 107:173–179 (1994).

*Primary Examiner*—Richard L. Raymond
*Attorney, Agent, or Firm*—Hale and Dorr LLP

[57] ABSTRACT

A compound comprising a non-steroidal antiinflammatory agent to which is directly or indirectly linked an NO group, a compound comprising an enolic anilide non-steroidal antiinflammatory agent to which is directly or indirectly linked an $NO_2$ group, a pharmaceutical composition including the compounds and methods of treatment of pain and/or inflammation using the compounds and compositions are disclosed. Also disclosed is a composition comprising a non-steroidal antiinflammatory agent and a compound that donates, transfers or releases nitric oxide.

29 Claims, 2 Drawing Sheets

NITROSO ESTERS OF β-OXO-AMIDES AND ARYL PROPIONIC ACID DERIVATIVES OF NON-STEROIDAL ANTIINFLAMMATORY DRUGS

This application is a continuation of U.S. application Ser. No. 09/235,802, filed Jan. 22, 1999, issued as U.S. Pat. No. 6,043,232, which is a divisional of application Ser. No. 08/899,238, filed Jul. 23, 1997, abandoned, which is a divisional of application Ser. No. 08/425,090, filed Apr. 19, 1995, issued as U.S. Pat. No. 6,051,588.

This invention relates to the field of non-steroidal antiinflammatory drugs (NSAIDS), particularly such drugs which have significantly reduced gastrointestinal side effects.

BACKGROUND OF THE INVENTION

Arena et al., WO94/12463, discloses the chemistry and pharmacology of nitroxybutylester [$(CH_2)_4$—$ONO_2$] derivatives of several aryl propionic acid non-steroidal antiinflammatory drugs including ketoprofen, flurbiprofen, suprofen, indobufen and etodolac. Studies on nitroxybutylester derivatives of flurbiprofen and ketoprofen are also reported in Wallace et al., *Gastroenterology*, 107:173–179 (1994). See, also, Cuzzolin et al., *Pharmacol. Res.*, 29(1):89–97 (1994); Reuter et al., *Life Sci. (USA)*, 55/1 (PL1–PL8) (1994); Reuter et al., *Gastroenterology*, 106(4):Suppl. A759 (1994); Wallace et al., *Eur. J. Pharmacol.*, 257(3):249–255 (1994); Wallace et al., *Gastroenterology*, 106(4):Suppl. A208 (1994); and Conforti et al., *Agents-Actions*, 40(3–4):176–180 (1993). These publications uniformly examine and rely upon the use of indirectly linked nitrogen dioxide substitutions.

SUMMARY OF THE INVENTION

The present invention is based on the discovery by the inventors that it is possible to directly or indirectly link a nitrogen monoxide group, nitric oxide (NO), to a non-steroidal antiinflammatory agent and that the resulting compounds not only possess potent analgesic/antiinflammatory properties but has a much reduced potential for producing gastrointestinal lesions (ulcers).

In one aspect the present invention provides a compound comprising a non-steroidal antiinflammatory agent to which is directly or indirectly linked an NO group. The non-steroidal antiinflammatory agent can, for example, be an aryl propionic acid or, more preferably, an enolic anilide. The invention also provides compositions comprising such compounds in a pharmaceutically acceptable carrier.

In another aspect the invention provides a composition comprising a non-steroidal antiinflammatory agent and a compound that donates, transfers or releases nitric oxide.

In another aspect the invention provides a method treating pain and/or inflammation in an animal in need thereof by administering to the animal a pain and/or inflammation reducing amount of a composition of the invention.

In another aspect, the present invention describes a compound comprising an enolic anilide non-steroidal antiinflammatory agent to which is directly or indirectly linked an $NO_2$ group to form an enolic ether.

BRIEF DESCRIPTION OF THE DRAWINGS

FIG. 2 ALSO illustrates that doses up to μmol/kg of NO-piroxicam did not produce significant lesions compared to the vehicle control as described in Example 4.

DETAILED DESCRIPTION OF THE INVENTION

Figure 1:
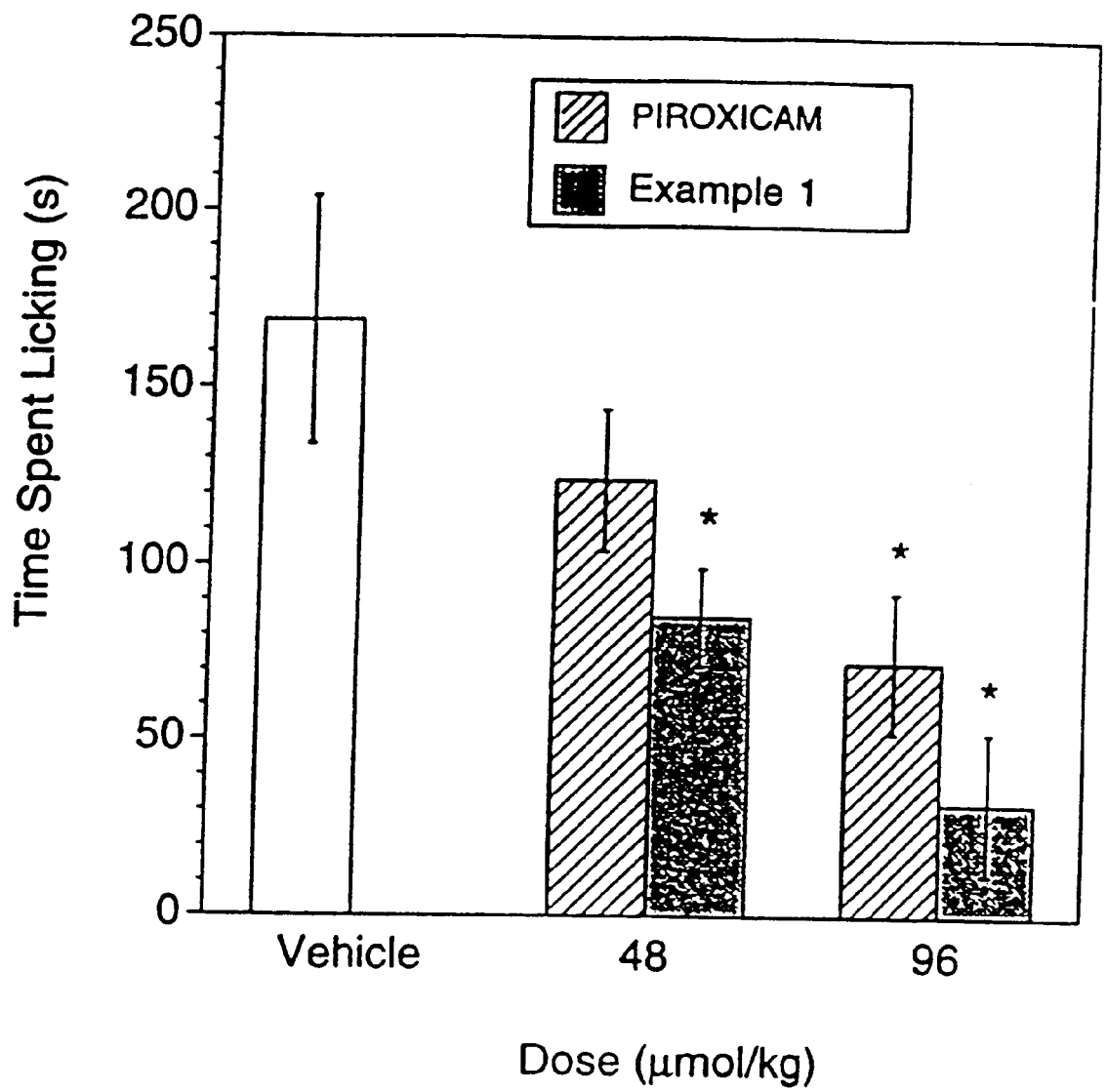
FIG. 1 illustrates the data which show that NO-piroxicam inhibited the paw lick response with greater potency than piroxicam, itself, as described in Example 3.

Nitrogen monoxide can exist in three forms: NO. (nitroxyl), NO., (nitric oxide) and $NO^+$ (nitrosonium). NO. is a highly reactive short-lived species that is potentially toxic to cells. This is critical, because the pharmacological efficacy of NO depends upon the form in which it is delivered. In contrast to NO·, nitrosonium and nitroxyl do not react with $O_2$ or $O_2^·$ species, and are also resistant to decomposition in the presence of redox metals. Consequently, administration of NO equivalents does not result in the generation of toxic by-products or the elimination of the active NO moiety.

The NSAID can be nitrosylated through sites such as oxygen(hydroxyl condensation), sulfur (sulphlydryl condensation), carbon and nitrogen.

One embodiment of the present invention is nitroso substituted compounds of the formula:

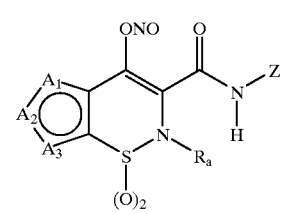

I wherein $R_a$ is lower alkyl, cycloalkyl, aryl or heteroaryl;

Z is an aryl or heteroaryl; and $A_1$, $A_2$ and $A_3$ comprise the other subunits of a 5- or 6-membered monocyclic aromatic ring and each is independently selected from (1) C—$R_1$ wherein $R_1$ at each occurrence is independently selected from hydrogen, lower alkyl, lower haloalkyl, alkoxyalkyl, halogen or nitro; (2) N—$R_d$ wherein $R_d$ at each occurrence is independently selected from a covalent bond to an adjacent ring atom in order to render the ring aromatic, hydrogen, lower alkyl, cycloalkyl, arylalkyl, aryl, heteroaryl; (3) sulfur; (4) oxygen; and (5) $B_a$=$B_b$ wherein $B_a$ and $B_b$ are each independently selected from nitrogen or C—$R_1$ wherein at each occurrence $R_1$ is as defined above.

Another embodiment of the present invention is nitroso substituted compounds of the formula:

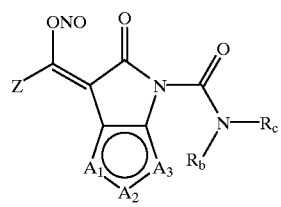
(II)
wherein
- $R_b$ and $R_c$ are each independently selected from hydrogen, lower alkyl, cycloalkyl, arylalkyl, aryl, heteroaryl; and
- $Z$, $A_1$, $A_2$, $A_3$ are defined as above.
Another embodiment of the invention is compounds of the formula:
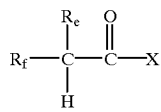
wherein
- $R_c$ is hydrogen or lower alkyl;
- $R_f$ is selected from
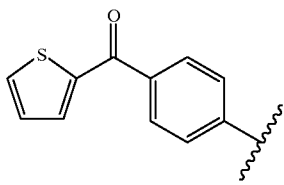
(1)
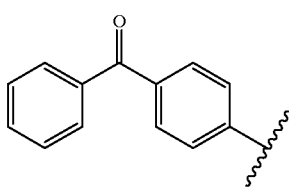
(2)
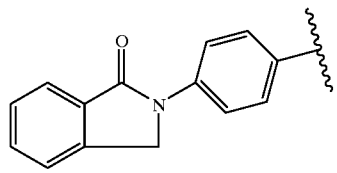
(3)
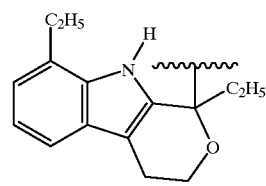
(4)
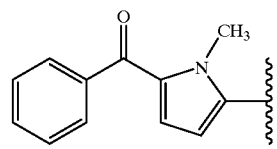
(5)
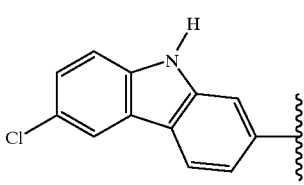
(6)
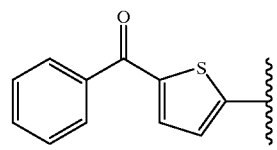
(7)
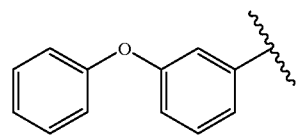
(8)
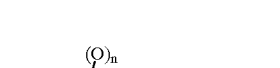
(9)
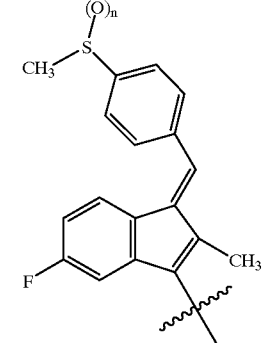
(10)
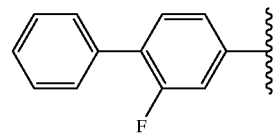
(11)

-continued

(12)
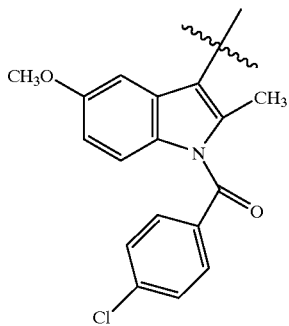

(13)
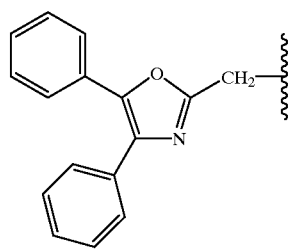

(14)
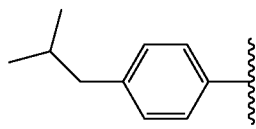

(15)
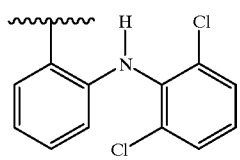

in which
n is 0 or 1; and

X is (1) —Y—[(R$_b$) (R$_c$)]$_p$—T—NO, in which Y is oxygen, sulfur or N—R$_i$ in which R$_i$ is hydrogen or lower alkyl, R$_b$ and R$_c$ are defined as above, p is an integer from 0 to 6 and T is a covalent bond, oxygen or sulfur; or (2)

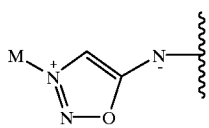

in which W is a heterocyclic ring or NR$_h$R$_i$ wherein R$_h$ and R$_i$ are independently selected from lower alkyl, aryl or alkenyl.

Another embodiment of the invention is compounds of the formula:

IV
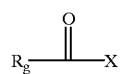

wherein

R$_g$ is selected from (1)
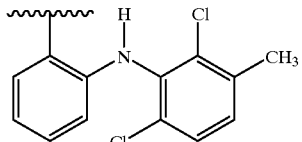

(2)
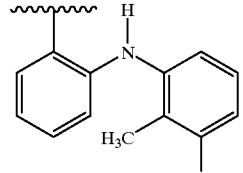

(3)
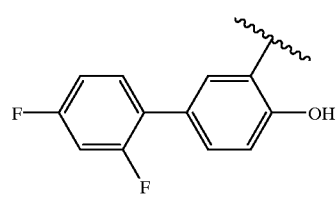

(4)
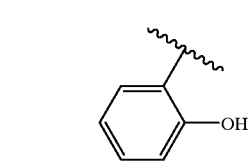

(5)
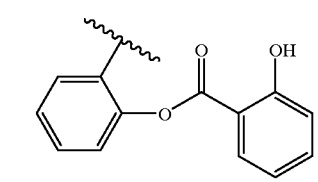

(6)

and X is defined as above.

The present invention also relates to processes for preparing the compounds of formula (I), (II), (III) or (IV) and to the intermediates useful in such processes.

The term "lower alkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to RO- wherein R is loweralkyl as defined above. Representative examples of alkoxy groups include methoxy, ethoxy, t-butoxy and the like The term "alkoxyalkyl" as used herein refers to a alkoxy group as previously defined appended to an alkyl group as previously defined. Examples of alkoxyalkyl include, but are not limited to, methoxymethyl, methoxyethyl isopropoxymethyl and the like.

The term "alkenyl" as used herein refers to a branched or straight chain C$_2$–C$_{10}$ hydrocarbon.

The term "amino" as used herein refers to —NH$_2$.

The term "alkylamino" as used herein refers to R$_1$NH- wherein R$_1$ is a loweralkyl group, for example methylamino, ethylamino, butylamino, and the like.

The term "dialkylamino" as used herein refers to R$_2$R$_3$N- wherein R$_2$ and R$_3$ are independently selected from loweralkyl, for example dimethylamino, diethylamino, methyl propylamino, and the like.

The term "nitro" as used herein refers to the group —NO$_2$.

The term "nitroso" as used herein refers to the group —NO.

The term "aryl" as used herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substitued with one, two or three substituents independently selected from loweralkyl, haloalkyl, alkoxy, amino, alkylamino, dialkylamino, hydroxy, halo, and nitro. In addition, substitued aryl groups include tetrafluorophenyl and pentafluorophenyl.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "halogen" or "halo" as used herein refers to I, Br, Cl, or F. The term "haloalkyl" as used herein refers to a lower alkyl radical, as defined above, bearing at least one halogen substituent, for example, chloromethyl, fluoroethyl or trifluoromethyl and the like.

The term "heteroaryl" as used herein refers to a mono- or bi- cyclic ring system containing one or two aromatic rings and containing at least one nitrogen, oxygen, or sulfur atom in an aromatic ring. Heteroaryl groups (including bicyclic heteroaryl groups) can be unsubstitued or substituted with one, two, or three substituents independently selected from loweralkyl, haloalkyl, alkoxy, amino, alkylamino, dialkylaminon hydroxy, halo and nitro. Examples of heteroaryl groups include not limited to pyridine, pyrazine, pyrimidine, pyridazine, pyrazole, triazolen thiazole, isothiazole, benzothiazole, benzoxazole, thiadiazole, oxazole, pyrrole, imidazole, and isoxazole.

The term "heterocyclic ring" refers to any 3-, 4-, 5-, 6-, or 7-membered nonaromatic ring containing at least one nitrogen atom which is bonded to an atom which is not part of the heterocyclic ring. In addition, the heterocyclic ring may also contain a one additional heteroatom which may be nitrogen, oxygen, or sulfur.

Compounds of the invention which have one or more asymmetric carbon atoms may exist as the optically pure enantismers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Some of the compounds of the present invention may be synthesized as shown in reaction Schemes I through VIII presented below, in which R$_a$, R$_b$, R$_c$, R$_d$, R$_f$, R$_g$, A$_1$, A$_2$, A$_3$, m, n, x and Z are as defined above or as depicted in the reaction schemes for formulas I, II, III or IV; P$^1$ is an oxygen protecting group and P$^2$ is a sulfur protecting group. The reactions are performed in solvents appropriate to the reagents and materials employed are suitable for the transformations being effected. It is understood by those skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur and oxygen—protecting groups is well known in the art for protecting thiol, alcohol, and amino groups against undesirable reactions during a synthetic procedure and many such protecting groups are known, c.f., T. H. Greene and P. G. M. Wuts, *Protective Groups in Organic Synthesis*, John Wiley & Sons, New York (1991).

Nitroso compounds of formula I wherein A$_1$, A$_2$, A$_3$, R$_a$, and Z are defined as above may be prepared according to reaction Scheme 1. The enolic form of the keto amide 1 is reacted with a suitable nitrosylating agent such as thionyl chloride nitrite, thionyl dinitrite [c.f., Hakimelahi et. al., *Helvetica Chimica Acta*. 67, 907 (1984)], or nitrosium tetrafluoroborate with or without an amine base such as pyridine or triethylamine in a suitable anhydrous solvent such as tetrahydrofuran (THF), dimethylforamide (DMF), or acetonitrile to afford the O-nitrite I.

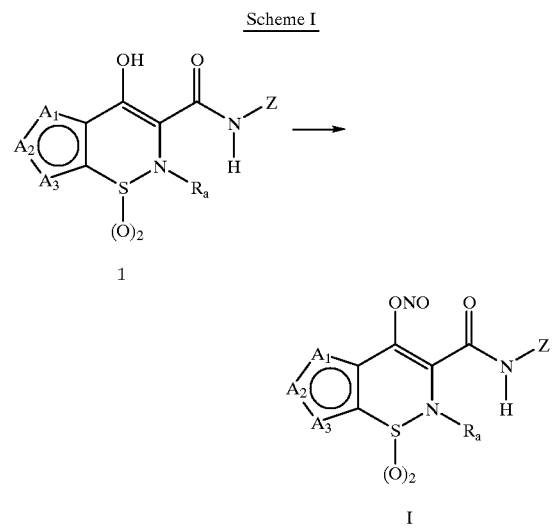

Scheme I

Nitroso compounds of formula II wherein A$_1$, A$_2$, A$_3$, R$_b$, R$_c$ and Z are defined as above may be prepared according to reaction Scheme II. The enolic form of the β-keto amide 2 is reacted with a suitable nitrosylating agent such as thionyl chloride nitrite, thionyl dinitrite, or nitrosium tetrafluoroborate with or without an amine base such as pyridine or triethylamine in a suitable anhydrous solvent such as THF, DMF, or acetonitrile to afford the O-nitrite II.

Scheme II

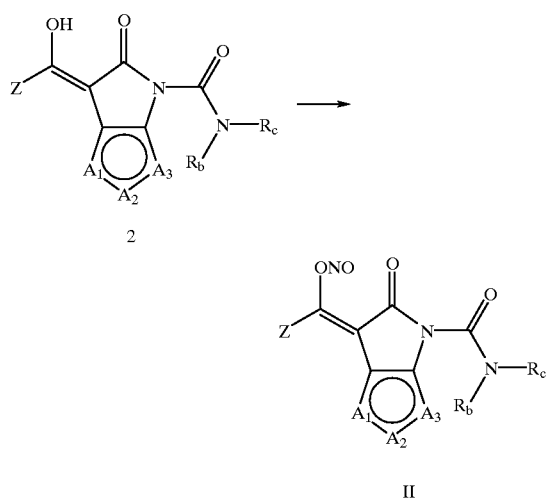

Nitroso compounds of formula III wherein $R_c$ and $R_f$ are defined as above and an O-nitrosylated ester is representative of the X group as defined above may be prepared according to Scheme III. An acid 3 is converted into the ester 4 wherein $R_b$ and $R_c$ are defined as above by reaction with an appropriate monoprotected diol. Preferred methods for the preparation of esters are initially forming the mixed anhydride via reaction of 3 with a chloroformate such as isobutylchloroformate in the presence of a non nucleophilic base such as triethylamine in an anhydrous inert solvent such as diethylether or THF. The mixed anhydride is then reacted with the monoprotected alcohol preferably in the presence of a condensation catalyst such as 4-dimethylamine pyridine. Alternatively, acid 3 and monoprotected diol may be coupled to afford 4 by treatment with a dehydration agent such as dicyclohexylcarbodiimide (DCC). Alternatively, acid 3 may be first converted into an alkali metal salt such as the sodium, potassium, or lithium salt, which is then reacted with an alkyl halide which also contains a protected hydroxyl group in an polar solvent such as DMF to afford 4. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate with or without an amine base such as pyridine or triethylamine in a suitable anhydrous solvent such as THF, DMF, or acetonitrile affords the compound of the formula IIIA.

Scheme III

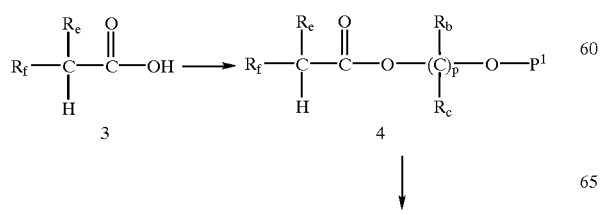

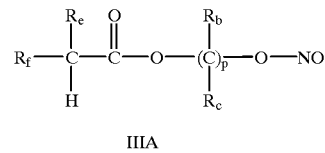

IIIA

Nitroso compounds of formula III wherein $R_c$ and $R_f$ are defined as above and a S-nitrosylated ester is representative of the X group as defined above may be prepared according to Scheme IV. An acid 3 is converted into ester 5 by reaction with an appropriate protected thiol containing alcohol. Preferred methods for the preparation of esters are initially forming the mixed anhydride via reaction of 3 with a chloroformate such as isobutylchloroformate in the presence of a non nucleophilic base such as triethylamine in an anhydrous inert solvent such as diethylether or THF. The mixed anhydride is then reacted with the protected thiol containing alcohol preferably in the presence of condensation catalyst such as 4-dimethylamine pyridine. Altenatively, the acid and protected thiol containing alcohol may be coupled to afford 5 by treatment with a dehydration agent such as DCC. Alternatively, acid 3 may be first converted into an alkali metal salt such as the sodium, potassium, or lithium salt, which is then reacted with an alkyl halide which also contains a protected thiol group in an polar solvent such as DMF to afford 5. Preferred protecting groups for the thiol moiety as a disulfide, as a thiocarbamate such as N-methoxymethyl thiocarbamate or as a thiol ester such as thiolacetate tiobenzoate. Deprotection of the thiol moiety (zinc in dilute aqueous acid, triphenylphosphine in water and sodium borohydride are preferred methods for reducing disulfide groups while aqueous base is typically are utilized to hydrolyze N-methoxymethyl thiocarbamates) followed by reaction a suitable nitrosylating agent such as thionyl chloride nitrite, thionyl dinitrite, or nitrosium tetrafluoroborate in a suitable anhydrous solvent such as THF, DMF, or acetonitrile or sodium nitrite is aqueous acid affords the compound of the formula IIIB.

Scheme IV

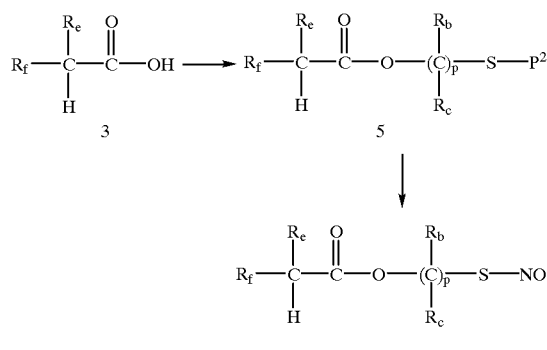

Nitroso compounds of formula III wherein $R_c$ and $R_f$ are defined as above and a 3-W-substituted sydnonimine wherein W is as defined above is representative of the X group as defined above may be prepared according to Scheme V. An acid 3 is converted into the carboximide IIIC by reaction with a 3-W-substituted sydnonimine. Preferred methods for the preparation of carboximides are initially forming the mixed anhydride via reaction of 3 with a chloroformate such as isobutylchloroformate in the presence of a non nucleophilic base such as triethylamine in an anhydrous inert solvent such as diethylether or THF. The mixed anhydride is then reacted with the 3-W-substituted sydnonimine to afford IIIC. Alternatively, the acid 3 may be coupled to the 3-W-substituted sydnonimine to afford IIIC by treatment with a dehydration agent such as DCC. Alternatively, acid 3 may be converted into an active ester by reaction with a suitably substituted phenol utilizing any of the conditions for ester formation described for Scheme 1, followed by reaction with the a 3-W-substituted sydnonimine. Preferred 3-W-substituted sydnonimines are 1,2,3,4-oxatriazolium, 5-amino-3-morpholine and 1, 2, 3, 4-oxatriazolium, 5-amino-3-(3-chloro-2-methyl-benzene) and preferred active esters are para-nitrophenyl, 2,4,5-trichlorophenyl, and pentafluorophenyl.

Scheme V

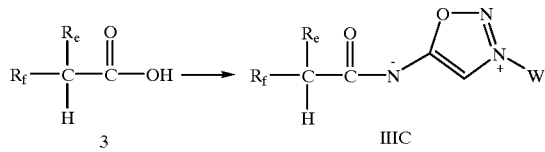

Nitroso compounds of formula IV wherein Rg is defined as above and an 0-nitrosylated ester is representative of the group as defined above may be prepared according to Scheme VI. An acid 6 is converted into ester 7 wherein $R_b$ and $R_c$ are as defined above, by reaction with an appropriate monoprotected diol. Preferred methods for the preparation of esters are initially forming the mixed anhydride via reaction of 6 with a chloroformate such as isobutylchloroformate in the presence of a non nucleophilic base such as triethylamine in an anhydrous inert solvent such as diethylether or THF. The mixed anhydride is then reacted with the monoprotected diol preferably in the presence of a condensation catalyst such as 4-dimethylamine pyridine. Alternatively, acid 6 first may be converted to the acid chloride be treatment with oxalyl chloride in the presence of a catalytic amount of DMF. The acid chloride is then reacted with the monoprotected alcohol preferably in the presence of a condensation catalyst such as 4-dimethylamine pyridine and a tertiary amine base such as triethyl amine to afford ester 7. Alternatively, acid 6 and monoprotected diol may be coupled to afford 7 by treatment with a dehydration agent such as DCC. Alternatively, acid 6 first may be converted into an alkali metal salt such as the sodium, potassium, or lithium salt, which is then reacted with an alkyl halide which also contains a protected hydroxyl group in an polar solvent such as DMF to afford 7. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate with or without an amine base such as pyridine or triethylamine in a suitable anhydrous solvent such as THF, DMF, or acetonitrile affords the compound of the formula IVA.

Scheme VI

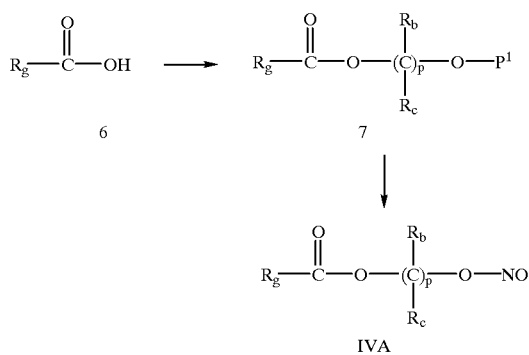

Nitroso compounds of formula IV wherein Rg is defined a above and a S-nitrosylated ester is representative of the X group as defined above may be prepared according to Scheme VII. An acid 6 is converted into ester 8 by reaction with an appropriate protected thiol containing alcohol. Preferred methods for the preparation of esters are initially forming the mixed anhydride via reaction of 6 with a chloroformate such as isobutylchloroformate in the presence of a non-nucleophilic base such as triethylamine in an anhydrous inert solvent such as diethylether or THF. The mixed anhydride is then reacted with the protected thiol containing alcohol preferably in the presence of a condensation catalyst such a 4-dimethylamine pyridine. Alternatively, acid 6 first may be converted to the acid chloride be treatment with oxalylchloride in the presence of a catalytic amount of DMF. The acid chloride is then reacted with the protected thiol containing alcohol preferably in the presence of a condensation catalyst such as 4-dimethylamine pyridine and a tertiary amine base such as triethyl amine to afford ester 8. Alternatively, the acid and protected thiol containing alcohol may be coupled to afford 8 by treatment with a dehydration agent such as DCC. Alternatively, acid 6 first may be converted into an alkali metal salt such as the sodium, potassium, or lithium salt, which is then reacted with an alkyl halide which also contains a protected thiol group in an polar solvent such as DMF to afford 8. Preferred protecting groups for the thiol moiety as a disulfide, as a thiocarbamate such as N-methoxymethyl carbamate or as a thiolester thiol acetate. Deprotection of the thiol moiety (zinc in dilute aqueous acid, triphenylphosphine in water and sodium borohydride are preferred methods for reducing disulfide groups while aqueous base is typically utilized to hydrolyze N-methoxymethyl thiocarbamates and thiol esters) followed by reaction a suitable nitrosylating agent such as thionyl chloride nitrite, thionyl dinitrite, or nitrosium tetrafluoroborate with or without an amine base such as pyridine or triethylamine in a suitable anhydrous solvent such as THF, DMF, or acetonitrile or sodium nitrite it is aqueous acid affords the compound of the formula IVB.

Scheme VII

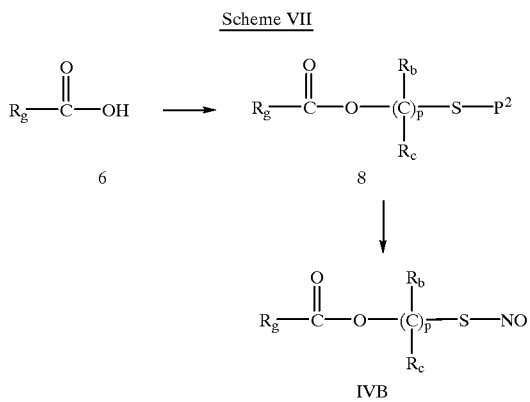

Nitroso compounds of formula IV wherein Rg is defined as above and a 3-substituted sydnonimine is representative of the X group as defined above may be prepared according to Scheme VIII. An acid 6 is converted into the carboximide IVC by reaction with a 3-W-substituted sydnonimine wherein W is as defined above. Preferred methods for the preparation of carboximides are initially forming the mixed anhydride via reaction of 6 with a chloroformate such as isobutylchloroformate in the presence of a non nucleophilic base such as triethylamine in an anhydrous inert solvent such as diethylether or THF. The mixed anhydride is then reacted with the 3-W-substituted sydnonimine to afford IVC. Alternatively, the acid 6 may be coupled to the 3-W-substituted sydnonimine to afford IVC by treatment with a dehydration agent such as DCC. Alternatively, acid 6 may be converted into an active ester by reaction with a suitably substituted phenol utilizing any of the conditions for ester formation described above, followed by reaction with the a 3-W-substituted sydnonimine. Preferred 3-W-substituted sydnonimines are 1,2,3,4-oxatriazolium, 5-amino-3-morpholine and 1,2,3,4- oxatriazolium, 5-amino-3-(3-chloro-2-methyl-benzene) and preferred active esters are para-nitrophenyl, 2,4,5-trichlorophenyl, and pentafluorophenyl.

Scheme VIII

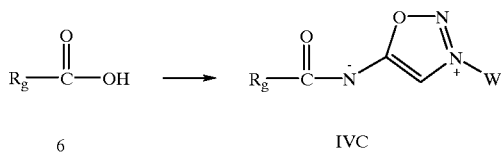

In another aspect, the present invention describes a compound comprising an enolic anilide non-steroidal antiinflammatory agent to which is directly or indirectly linked an $NO_2$ group to form an enolic ether.

Numerous examples of compounds that donate, transfer or release nitric oxide are disclosed, for example, in U.S Pat. Nos. 5,002,964; 5,025,001; 5,187,183; 5,356,890 5,380,758; and 5,385,937, and also in PCT Published Application No. WO 93/09806, each of which is incorporated by reference herein.

Another aspect the invention provides a method of treating pain in an individual in need thereof which comprises treating an individual for pain by administering to the individual an analgesic amount of a composition comprising a compound of the invention in a pharmaceutically acceptable carrier.

Another aspect the invention provides a method of treating an inflammatory disorder in an individual in need thereof which comprises treating an individual for an inflammatory disorder by administering to the individual an antiinflammatory amount of a composition comprising a compound of the invention in a pharmaceutically acceptable carrier.

The compounds and compositions of the present invention are novel and can be utilized to treat numerous inflammatory disease states and disorders. For example, reperfusion injury to an ischemic organ, e.g., reperfusion injury to the ischemic myocardium, myocardial infarction, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, disseminated intravascular coagulation, fatty embolism, adult and infantile respiratory distress, carcinogenesis and hemorrhages in neonates.

A further aspect of the present invention provides pharmaceutical compositions which comprise a compound of the present invention in combination with a pharmaceutically acceptable carrier.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1, 3-butanediol. Among the acceptable vehicles and solvents that may be employed are water, Ringer's solution, and isotonic sodium chloride solution. In addition, sterile, fixed oils are conventionally employed an a solvent or suspending medium. For this purpose any bland fixed oil may be employed including synthetic mono- or diglycerides. in addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

EXAMPLE 1

4-Nitrite-2-Methyl-N-2-Pyridinyl-2-H-1,2-Benzothiazine-2-Carboxamide-1,1-Dioxide Method A Under a nitrogen atmosphere, 1.1 mL (0.015 mol) of thionyl chloride was added dropwise to 4.5 grams (0.03 mol) of a silver nitrite slurry in 40 mL of THF at 0° C. The resultant yellow-orange mixture was stirred in ice 30 minutes. A solution of 1.6 grams (0.005 mol) of piroxicam in 50 mL of THF was added dropwise. The reaction was stirred in ice 1 hour followed by 2 hours at room temperature. The mixture was poured into 150 mL of cold, saturated sodium bicarbonate solution. The organic phase was separated, washed with saturated sodium chloride and dried over magnesium sulfate. Concentration in vacuo afforded 1.6 grams of a yellow solid, which consisted of a mixture of starting material and product. Treatment of a methylene chloride solution of the solid with decolorizing charcoal, followed by concentration and recrystallization from acetonitrite afforded 490 mg of a white solid, which melted with decomposition at 190° C. after beginning to darken at 180° C.

Method B

To a solution of piroxicam (1.5 g, 4.53 mmol) in anhydrous dichloromethane(20 ml) was added pyridine (467 mg, 5.9 mmol) and nitrosonium tetrafluoroborate (687 mg, 5.9 mmol). The reaction mixture was stirred at room temperature 72 hours after which time the orange heterogeneous mixture was poured onto saturated aqueous sodium bicarbonate. The organic phase was separated and the aqueous phase was extracted with additional dichloromethane (X1). The combined organic phases were dried over sodium sulfate and the solvent was evaporated in vacuo. The residue was dissolved in ethyl acetate and treated with decolorizing charcoal. Filtration, followed by precipitation of the product (title compound) by the addition of ether afforded 403 mg of a slightly beige solid as crop 1 with an additional 13 mg as crop 2.

EXAMPLE 2

Comparative Analgesic/Antiinflammatory Activities

The title compound of Example 1 was tested side-by-side with piroxicam and vehicle to evaluate its analgesic/antiinflammatory activities. The mouse formalin paw lick test (Hunskaar and Hole, *Pain,* 30:103, 1987) was used for the determination of analgesic/antiinflammatory activities.

Male CD-1 mice (Charles River Laboratories, Wilmington, Mass.) weighing 26–30 g were used for the formalin test. Drugs were dissolved in dimethylsulfoxide (DMSO) immediately prior to injection. Mice were injected subcutaneously with 30 µL of piroxicam, the title compound of Example 1 or vehicle. Thirty minutes later, 20 µL of 1% formalin was injected into the hind paw of each mouse. The time spent licking the injected paw was monitored for 25 minutes.

FIG. 1 shows that a 48 µmol/kg (16 mg/kg) dose of piroxicam and a 48 µmol/kg dose of the title compound of Example 1 significantly inhibited the paw lick response induced by a nociceptive stimulus (P<0.05). Piroxicam inhibited the paw lick response between 10–25 minutes by 71% while an equivalent dose of the title compound of Example 1 inhibited the response by 89%. Thus, the title compound of Example 1 is even more potent than piroxicam in producing the analgesic/antiinflammatory activities.

EXAMPLE 3

Comparative Gastric Lesion Potentials

The title compound of Example 1 was tested side-by-side with piroxicam and vehicle to evaluate its potential to produce gastric lesion. The rat gastric lesion test (Kitagawa et al., *J. Pharmacol. Exp.,* 253:1133, 1990; Al-Ghamdi et al., *J. Int. Med. Res.,* 19:242, 1991) was used to evaluate the potential to produce gastric lesion.

Male Sprague Dawley rats (Charles River Laboratories, Wilmington, Mass.) weighing 230–250 g were used for the experiments. The rats were housed for at least five days with laboratory chow and water ad libitum prior to the study. The rats were then fasted for 30 hours with free access to water and then dosed orally with vehicle (10% DMSO in Tris HCl buffer adjusted to pH 7.4 with NaOH) or with various doses of drugs given at a volume of 0.5 mL/100 g. Piroxicam and the title compound of Example 1 were dissolved in DMSO and then diluted in Tris buffer (pH 7.4) immediately before dosing. Eighteen hours after dosing, rats were euthanized by $CO_2$ and the stomachs were dissected. The stomachs were dissected along the greater curvature, washed with a directed stream of cold 0.9% saline and pinned open on a sylgard based petridish for examination of the hemorrhagic lesion. Gastric lesion score was expressed in mm and calculated by the equation Lesion Score=$(n \times d_1)+(n \times d_2)+ \ldots \ldots +(n \times d_{10})$, where d is the maximum diameter of each lesion (ulcer) and n is the number of lesions of that size.

Figure 2:
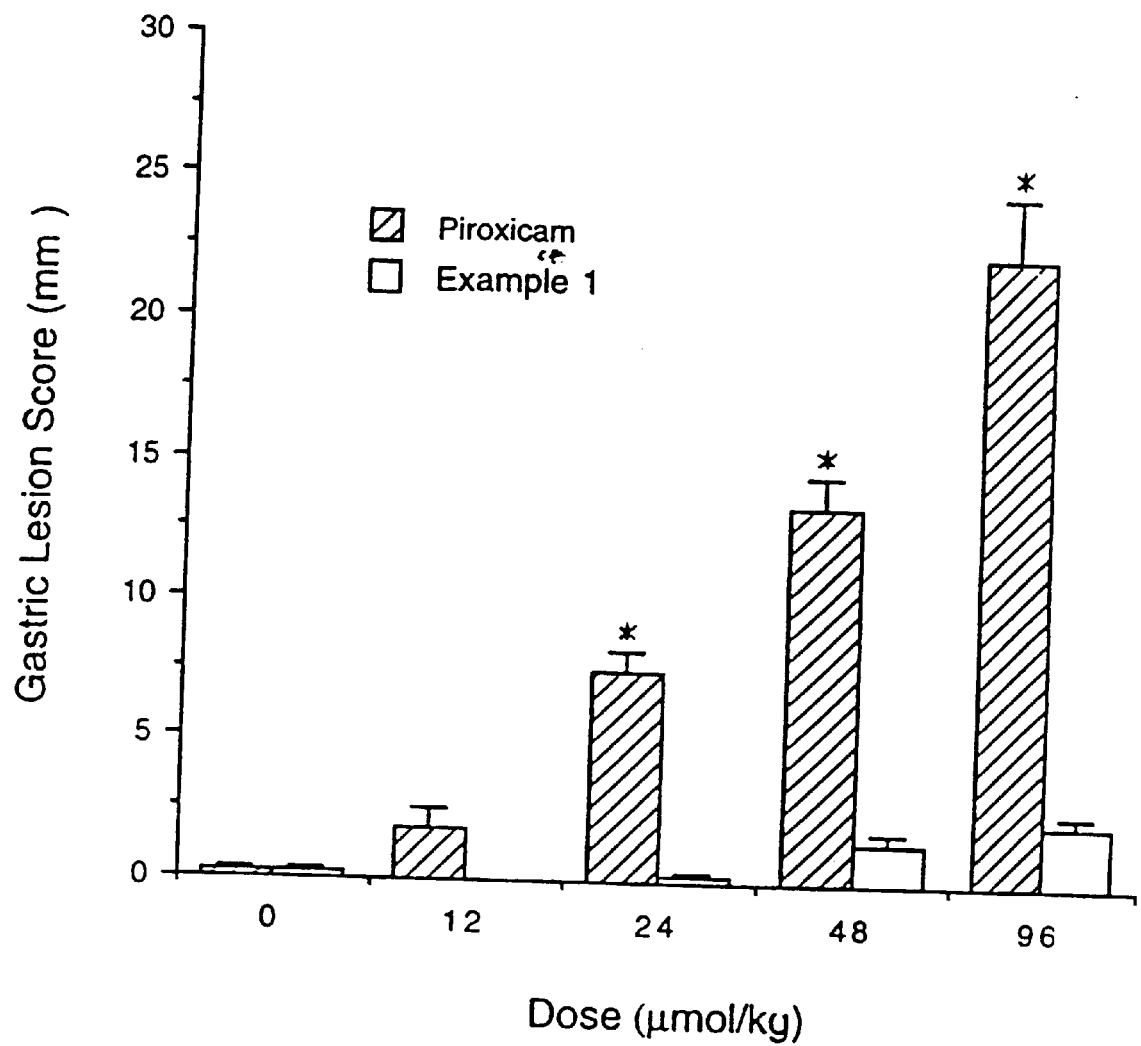
FIG. 2 illustrates that piroxicam at 24 and 48 μmol/kg produced very significant gastric lesions as described in Example 4.

FIG. 2 shows the dose response of piroxicam or producing gastric lesions. Piroxicam at 24 and 48 $\mu$mol/kg produced very significant gastric lesions. FIG. 3 shows that a 48 $\mu$mol/kg dose of the title compound of Example 1 produced significantly less gastric lesions than an equivalent dose of piroxicam. In fact, this 48 $\mu$mol/kg dose of NO-piroxicam produced less gastric lesions than a 4× lower dose of piroxicam and only produced slightly more lesions than the vehicle control. Thus NO-piroxicam has much reduced potential for producing gastric lesion compared to piroxicam.

What is claimed is:

1. An enolic anilide non-steroidal antiinflammatory drug having at least one $NO_2$ group in the form of an enolic ether.

2. A composition comprising the enolic anilide non-steroidal antiinflammatory drug of claim 1 and a pharmaceutically acceptable carrier.

3. A method for treating pain in an individual in need thereof comprising administering the composition of claim 2 to the individual.

4. A method for treating an inflammatory disorder in an individual in need thereof comprising administering the composition of claim 2 to the individual.

5. The method of claim 4, wherein the inflammatory disorder is reperfusion to an ischemic organ, a myocardial infarction, inflammatory bowel disease, rheumatoid arthritis, osteoarthritis, hypertension, psoriasis, an organ transplant rejection, organ preservation, impotence, a radiation-induced injury, asthma, atherosclerosis, thrombosis, platelet aggregation, metastasis, influenza, a stroke, a burn, a trauma, acute pancreatitis, pyelonephritis, hepatitis, an autoimmune disease, insulin-dependent diabetes mellitus, disseminated intravascular coagulation, a fatty embolism, adult respiratory distress, infantile respiratory distress, carcinogenesis, or a hemorrhage in a neonate.

6. A method for treating inflammatory bowel disease in an animal in need thereof comprising administering to the animal a therapeutically effective amount of the composition of claim 2.

7. A method of reducing the gastrointestinal toxicity of a nonsteroidal antiinflammatory drug comprising administering to an animal in need thereof a therapeutically effective amount of the composition of claim 2.

8. A composition comprising the enolic anilide non-steroidal antiinflammatory drug of claim 1 and a compound that donates, transfers or releases nitric oxide.

9. The composition of claim 8, further comprising a pharmaceutically acceptable carrier.

10. A method for treating pain in an individual in need thereof comprising administering the composition of claim 8 to the individual.

11. A method for treating an inflammatory disorder in an individual in need thereof comprising administering the composition of claim 8 to the individual.

12. The method of claim 11, wherein the inflammatory disorder is reperfusion to an ischemic organ, a myocardial infarction, inflammatory bowel disease, rheumatoid arthritis, osteoarthritis, hypertension, psoriasis, an organ transplant rejection, organ preservation, impotence, a radiation-induced injury, asthma, atherosclerosis, thrombosis, platelet aggregation, metastasis, influenza, a stroke, a burn, a trauma, acute pancreatitis, pyelonephritis, hepatitis, an autoimmune disease, insulin-dependent diabetes mellitus, disseminated intravascular coagulation, a fatty embolism, adult respiratory distress, infantile respiratory distress, carcinogenesis, or a hemorrhage in a neonate.

13. A method for treating inflammatory bowel disease in an animal in need thereof comprising administering to the animal a therapeutically effective amount of the composition of claim 8.

14. A method of reducing the gastrointestinal toxicity of a nonsteroidal antiinflammatory drug comprising administering to an animal in need thereof a therapeutically effective amount of the composition of claim 8.

15. A composition comprising a compound of formula IV and a compound that donates, transfers or releases nitric oxide, wherein the compound of formula IV is:

IV

wherein $R_g$ is (1)

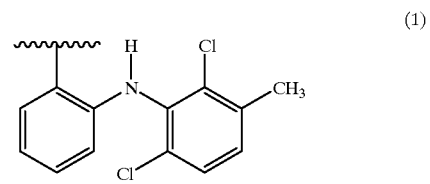

(2)

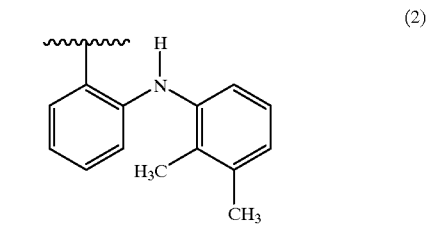

(3)

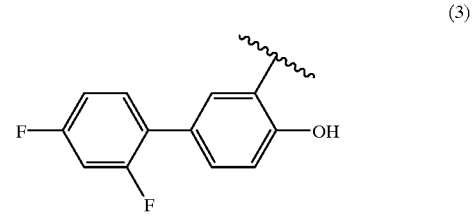

(4)

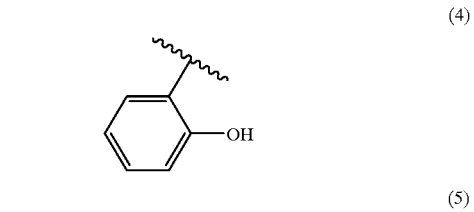

(5)

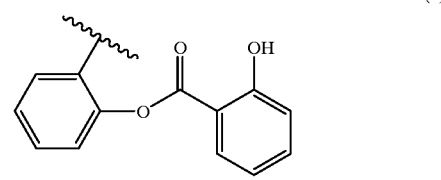

-continued (6)

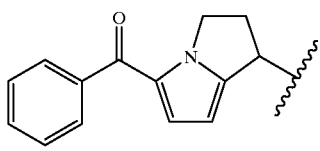

and X is:

(1) —Y—(C($R_b$)($R_c$))$_p$—T—NO, wherein Y is oxygen, sulfur or $NR_i$, wherein $R_i$ is a hydrogen atom or a lower alkyl group; $R_b$ and $R_c$ are each independently a hydrogen atom, a lower alkyl group, a cycloalkyl group, an arylalkyl group, an aryl group or a heteroaryl group; p is an integer from 0 to 6; and T is a covalent bond, oxygen or sulfur; or (2)

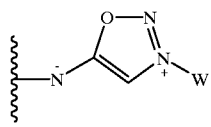

wherein W is a heterocyclic ring or $NR_hR_i$, wherein $R_h$ and $R_i$ are each independently a lower alkyl group, an aryl group or an alkenyl group.

16. The composition of claim 15, further comprising a pharmaceutically acceptable carrier.

17. A method for treating pain in an individual in need thereof comprising administering the composition of claim 16 to the individual.

18. A method for treating an inflammatory disorder in an individual in need thereof comprising administering the composition of claim 16 to the individual.

19. The method of claim 18, wherein the inflammatory disorder is reperfusion to an ischemic organ, a myocardial infarction, inflammatory bowel disease, rheumatoid arthritis, osteoarthritis, hypertension, psoriasis, an organ transplant rejection, organ preservation, impotence, a radiation-induced injury, asthma, atherosclerosis, thrombosis, platelet aggregation, metastasis, influenza, a stroke, a burn, a trauma, acute pancreatitis, pyelonephritis, hepatitis, an autoimmune disease, insulin-dependent diabetes mellitus, disseminated intravascular coagulation, a fatty embolism, adult respiratory distress, infantile respiratory distress, carcinogenesis, or a hemorrhage in a neonate.

20. A method for treating inflammatory bowel disease in an animal in need thereof comprising administering to the animal a therapeutically effective amount of the composition of claim 16.

21. A method of reducing the gastrointestinal toxicity of a nonsteroidal antiinflammatory drug comprising administering to an animal in need thereof a therapeutically effective amount of the composition of claim 16.

22. A composition comprising a compound of formula III and a compound that donates, transfers or releases nitric oxide, wherein the compound of formula III is:

III

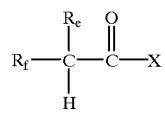

wherein $R_e$ is hydrogen or lower alkyl; and $R_f$ is:

(1)

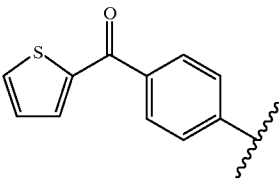

(2)

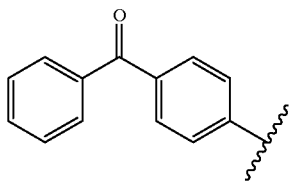

(3)

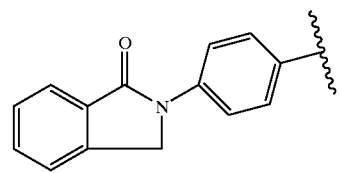

(4)

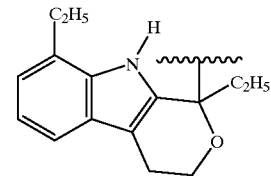

(5)

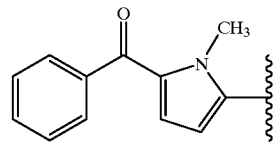

(6)

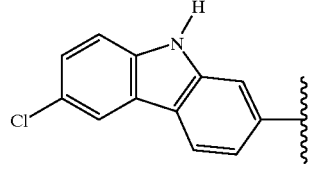

(7)

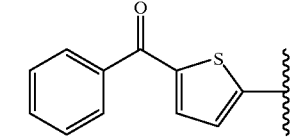

(8) 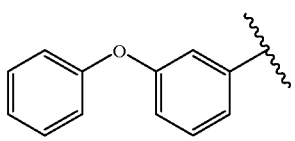

(9) 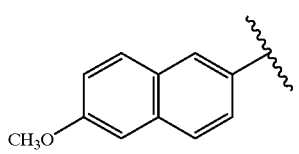

(10) 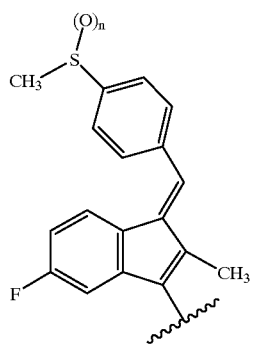

(11) 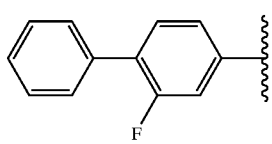

(12) 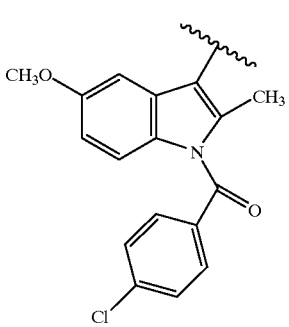

(13) 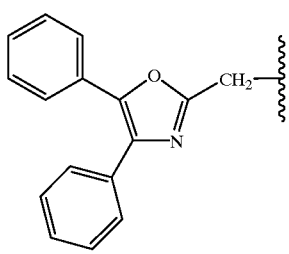

(14) 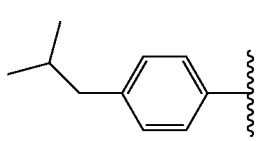

(15) 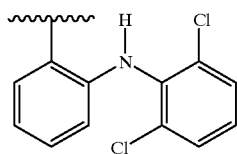

wherein n is 0 or 1; and X is:

(1) —Y—(C($R_b$)($R_c$))$_p$—T—NO, wherein Y is oxygen, sulfur or $NR_i$, wherein $R_i$ is a hydrogen atom or a lower alkyl group; $R_b$ and $R_c$ are each independently a hydrogen atom, a lower alkyl group, a cycloalkyl group, an arylalkyl group, an aryl group or a heteroaryl group; p is an integer from 0 to 6; and T is a covalent bond, oxygen or sulfur; or (2)

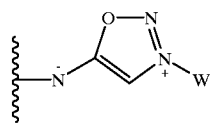

wherein W is a heterocyclic ring or $NR_hR_i$, wherein $R_h$ and $R_i$ are each independently a lower alkyl group, an aryl group or an alkenyl group.

23. The composition of claim 22, further comprising a pharmaceutically acceptable carrier.

24. A method for treating pain in an individual in need thereof comprising administering the composition of claim 23 to the individual.

25. A method for treating an inflammatory disorder in an individual in need thereof comprising administering the composition of claim 23 to the individual.

26. The method of claim 25, wherein the inflammatory disorder is reperfusion to an ischemic organ, a myocardial infarction, inflammatory bowel disease, rheumatoid arthritis, osteoarthritis, hypertension, psoriasis, an organ transplant rejection, organ preservation, impotence, a radiation-induced injury, asthma, atherosclerosis, thrombosis, platelet aggregation, metastasis, influenza, a stroke, a burn, a trauma, acute pancreatitis, pyelonephritis, hepatitis, an autoimmune disease, insulin-dependent diabetes mellitus, disseminated intravascular coagulation, a fatty embolism, adult respiratory distress, infantile respiratory distress, carcinogenesis, or a hemorrhage in a neonate.

27. A method for treating inflammatory bowel disease in an animal in need thereof comprising administering to the animal a therapeutically effective amount of the composition of claim 23.

28. A method of reducing the gastrointestinal toxicity of a nonsteroidal antiinflammatory drug comprising administering to an animal in need thereof a therapeutically effective amount of the composition of claim 23.

29. A method for treating inflammatory bowel disease in an animal in need thereof comprising administering to the animal a therapeutically effective amount of a composition comprising a compound of formula III and a pharmaceutically acceptable carrier, wherein the compound of formula III is:

III $$R_f-\overset{R_e}{\underset{H}{C}}-\overset{O}{C}-X$$

wherein $R_e$ is hydrogen or lower alkyl; and $R_f$ is:

(1) [thiophene-C(=O)-phenyl- group]

(2) [benzoyl-phenyl- group]

(3) [2-(1-oxoisoindolin-2-yl)phenyl- group]

(4) [ethyl-substituted pyrano-indole group with C₂H₅]

(5) [1-methyl-2-benzoylpyrrol-5-yl group]

(6) [6-chlorocarbazol-3-yl group]

(7) [2-benzoylthiophen-5-yl group]

(8) [3-phenoxyphenyl group]

(9) [6-methoxynaphthalen-2-yl group]

(10) [methylsulfonyl(oxide)phenyl-methylidene-fluoro-methylindene group]

(11) [2-fluorobiphenyl-4-yl group]

(12) [5-methoxy-2-methyl-1-(4-chlorobenzoyl)indol-3-yl group]

(13) [4,5-diphenyloxazol-2-yl-methylene group]

(14) [4-isobutylphenyl group]

(15)

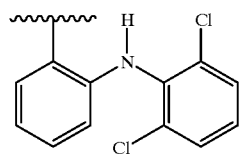

wherein n is 0 or 1; and X is:

(1) —Y—(C($R_b$)($R_c$))$_p$—T—NO, wherein Y is oxygen, sulfur or $NR_i$, wherein $R_i$ is a hydrogen atom or a lower alkyl group; $R_b$ and $R_c$ are each independently a hydrogen atom, a lower alkyl group, a cycloalkyl group, an arylalkyl group, an aryl group or a heteroaryl group; p is an integer from 0 to 6; and T is a covalent bond, oxygen or sulfur; or (2)

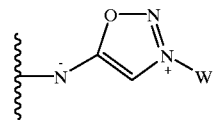

wherein W is a heterocyclic ring or $NR_hR_i$, wherein $R_h$ and $R_i$ are each independently a lower alkyl group, an aryl group or an alkenyl group.

* * * * *